US008880351B2

(12) United States Patent
Can et al.

(10) Patent No.: US 8,880,351 B2
(45) Date of Patent: Nov. 4, 2014

(54) METHOD AND APPARATUS FOR ANALYSIS OF TISSUE MICROARRAYS

(75) Inventors: Ali Can, Troy, NY (US); Michael John Gerdes, Albany, NY (US); Musodiq Olatayo Bello, Niskayuna, NY (US); Xiaodong Tao, Niskayuna, NY (US); Maximilian Seel, Boston, MA (US)

(73) Assignee: General Electric Company, Niskayuna, NY (US)

( * ) Notice: Subject to any disclaimer, the term of this patent is extended or adjusted under 35 U.S.C. 154(b) by 1733 days.

(21) Appl. No.: 12/055,121

(22) Filed: Mar. 25, 2008

(65) Prior Publication Data

US 2009/0247416 A1 Oct. 1, 2009

(51) Int. Cl.
*G01N 33/50* (2006.01)
*G06T 7/00* (2006.01)
*G01N 21/64* (2006.01)

(52) U.S. Cl.
CPC .......... *G01N 21/6452* (2013.01); *G06T 7/0024* (2013.01); *G06T 2207/30072* (2013.01)
USPC ......................................................... 702/19

(58) Field of Classification Search
None
See application file for complete search history.

(56) References Cited

PUBLICATIONS

"Simulate" definition, Merriam-Webster online dictionary, 2011, on the world wide web at http://www.merriam-webster.com/dictionary/simulate, 1 page.*
"Simulate" definition, 2009, on the world wide web at http://education.yahoo.com/reference/dictionary/entry/simulate, 1 page.*
A. Rabinovich, S. Krajewski, M. Krajewska, A. Skabaik, S. M. Hewitt, S. Belongie, J. C. Reed, and J. H. Price, "Framework for parsing, visualizing and scoring tissue microarray images," IEEE Trans. on Information Technology in Biomedicine, vol. 10, No. 2, pp. 209-219, 2006.
F. Demichelis, A. Sboner, M. Barbareschi, and R. Dellanna, "TMABoost: An integrated system for comprehensive management of tissue microarray data," IEEE Trans. on Information Technology in Biomedicine, vol. 10, No. 1, pp. 19-27, 2006.
W. Chen, M. Reiss, and D. J. Foran, "A prototype for unsupervised analysis of tissue microarrays for cancer research and diagnostics," IEEE Trans. on Information Technology in Biomedicine, vol. 8, No. 2, pp. 89-96, 2004.
http://biomax.us/faq.php; US Biomax, Inc. FAQs, 2008, 6 pages.

* cited by examiner

*Primary Examiner* — Jason Sims
(74) *Attorney, Agent, or Firm* — Fletcher Yoder, P.C.

(57) ABSTRACT

The present techniques include methods and systems for finding correspondences between tissue spots in tissue microarray serial sections belonging to the same recipient block. The present techniques may also be used to relate individual tissue cores to clinical information. Using either a whole slide image or the relative x-y coordinates of the tissue spots on the slide, individual tissue spots in different tissue microarrays may be linked to one another and their clinical information.

18 Claims, 10 Drawing Sheets

METHOD AND APPARATUS FOR ANALYSIS OF TISSUE MICROARRAYS

BACKGROUND

The invention relates generally to image processing and image analysis. More specifically, the present techniques relate to analysis of tissue microarrays made from serial sections of a multiple-tissue sample block.

Tissue microarrray (TMA) technology has become the standard in large-scale immunohistochemistry (IHC), fluorescent in situ hybridization (FISH), and mRNA in situ hybridization (RNA-ISH) studies for protein, DNA and RNA expression. To prepare the TMA slides, a tissue core is typically obtained from the patient tissue and inserted in a paraffin recipient block. The resulting recipient block typically has hundreds of tissue cores from multiple patients. This block may then be cut into sections that may be placed on glass slides for examination and imaging. In each of the serial sections, corresponding tissue cores belong to the same patient, and it is advantageous to be able to relate each patient core in one TMA slide to the corresponding one belonging to the same patient in another slide.

However, alignment of TMAs made from serial sections of the block is difficult. For example, the grid on the block is often not rectilinear, preventing simple alignment of multiple slides to line up individual samples. The misalignment is even more pronounced when each tissue core is imaged individually (in contrast to whole slide imaging where the entire slide is scanned into a single image). For example, in high-resolution fluorescent microscopy on TMAs, the microscope is manually or automatically moved to each core and a suitable region of the tissue core imaged. This makes the resulting grid even less rectilinear since the portion of the tissue imaged may vary slightly from core to core. In addition, it is common for a few tissue cores to fall off from the slides, and missing cores from one TMA slide are often different from those missing from another. However, in order to compare results between TMA slides made from the same block, it is advantageous to be able to link samples from the same patient.

Certain techniques focus on reducing the incidence of samples falling off of individual TMA slides. However, even if one tissue spot falls off, the correspondence between serial sections is lost and should be re-established before individual samples on the TMAs may be compared.

Other techniques for identifying samples on a TMA slide focus on one TMA and not on the use of multiple TMAs from adjacent sections. For example, a deformable mesh grid approach involves the user defining the number of rows and columns on the TMA and the software automatically generating a deformable mesh grid with the specified dimensions. The grid may be adjusted on a whole-slide image to match the layout of the spots on the TMA in a semi-automatic way, i.e., requiring some user intervention to adjust the grid. The elements of the grid can also be associated with TMA numbers to facilitate correlation with clinical information. This semi-automatic approach requires a whole slide image to be available and is not useful for imaging systems that do not produce whole slide images. Further, this system is not designed to correlate TMAs made from serial sections, and the loss of a number of spots on different slides may affect the deformable grid assignment. Other approaches, such as image-based approaches, analyze a whole slide image to identify the location of tissue cores on the slide and automatically generate a grid from the result of the analysis. These approaches require the tissue spots on the slide to confirm to a linear grid structure and do not correlate patient samples on one TMA to those on another TMA, or to relevant clinical information about the tissue spots.

BRIEF DESCRIPTION

The present techniques relate to methods and systems for finding correspondences between tissue spots in TMA slides that are made from the same recipient block. The present technique also provides the advantage of relating tissue core samples to clinical information. In addition, the present technique may be used with either whole slide images or the relative x-y coordinates of the tissue spots on the slide as inputs.

The present techniques provide a method for analyzing tissue microarrays, that includes: accessing respective images of two or more tissue microarrays, wherein the tissue microarrays are derived from the same recipient block, and wherein the tissue microarrays each comprise a respective plurality of tissue spots; registering the images; analyzing the position of each of the respective plurality of tissue spots of the tissue microarrays based on the registered images; and generating an output relating the tissue spots of the two or more tissue microarrays based on the analyzed positions.

The present techniques also include a computer-readable medium including instructions for: accessing respective images of two or more tissue microarrays, wherein the tissue microarrays are derived from the same recipient block, and wherein the tissue microarrays each comprise a respective plurality of tissue spots; registering the images; analyzing the position of each of the respective plurality of tissue spots of the tissue microarrays based on the registered images; and generating an output relating the tissue spots of the two or more tissue microarrays based on the analyzed positions.

The present techniques also include an image analysis system that includes a processor adapted to receive images of two or more tissue microarrays, wherein the tissue microarrays are derived from the same recipient block, and wherein the tissue microarrays each comprise a respective plurality of tissue spots. The processor adapted to run instructions for: registering the images; analyzing the position of each of the respective plurality of tissue spots of the tissue microarrays based on the registered images; and generating an output relating the tissue spots of the two or more tissue microarrays based on the analyzed positions.

The present techniques also include a tissue microarray map that includes: a registered image comprising images data from two or more tissue microarrays, wherein the tissue microarrays are derived from the same recipient block, and wherein the tissue microarrays each comprise a respective plurality of tissue spots; and tissue spots simulated on the registered image that were interpolated from analyzing the position of each of the respective plurality of tissue spots of the tissue microarrays based on the registered image and comparing those images to the recipient block.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The present techniques may determine correspondence between spots on TMAs in serial sections from the same recipient tissue block. For a given recipient block, there may be a TMA-map or other guide that indicates the layout of the spots in the block and the TMA number of each spot. The TMA numbers may represent patient IDs and/or other clinical information, which may include information related to the tissue samples from which the tissue spots were obtained. The present techniques may relate tissue cores with the TMA number and hence with clinical information. In addition to generating a visual representation of the correspondences of tissue spots from TMA serial sections, the correspondences may also be output as a spreadsheet file or other data format. The present techniques may use as input a whole slide image and/or the coordinates of the tissue spots as they are imaged.

The ability to relate tissue spots in adjacent TMAs or TMAs from the same recipient block to one another may be useful in correlating multiple biomarker expressions in immunohistochemistry studies. For example, a recipient block may generate a number of TMA slides. Each of these slides may be stained for expression of different biomarkers. Such a technique may be useful in studying complex diseases, such as cancer, and/or clinical conditions associated with multiple biomarkers. In addition, such techniques may be useful in investigating whether certain biomarkers are associated with a clinical condition. Because the recipient blocks may include many samples from a single patient, for example samples taken from different tissue sources or from normal tissue as well as tumor tissue, multiple biomarkers may be assessed across a variety of tissue types in a single patient with the present techniques. In addition, a recipient block may also include tissue samples from multiple patients. In other embodiments, multiple biomarkers may be evaluated in many patients in a relatively high-throughput manner.

Figure 1:
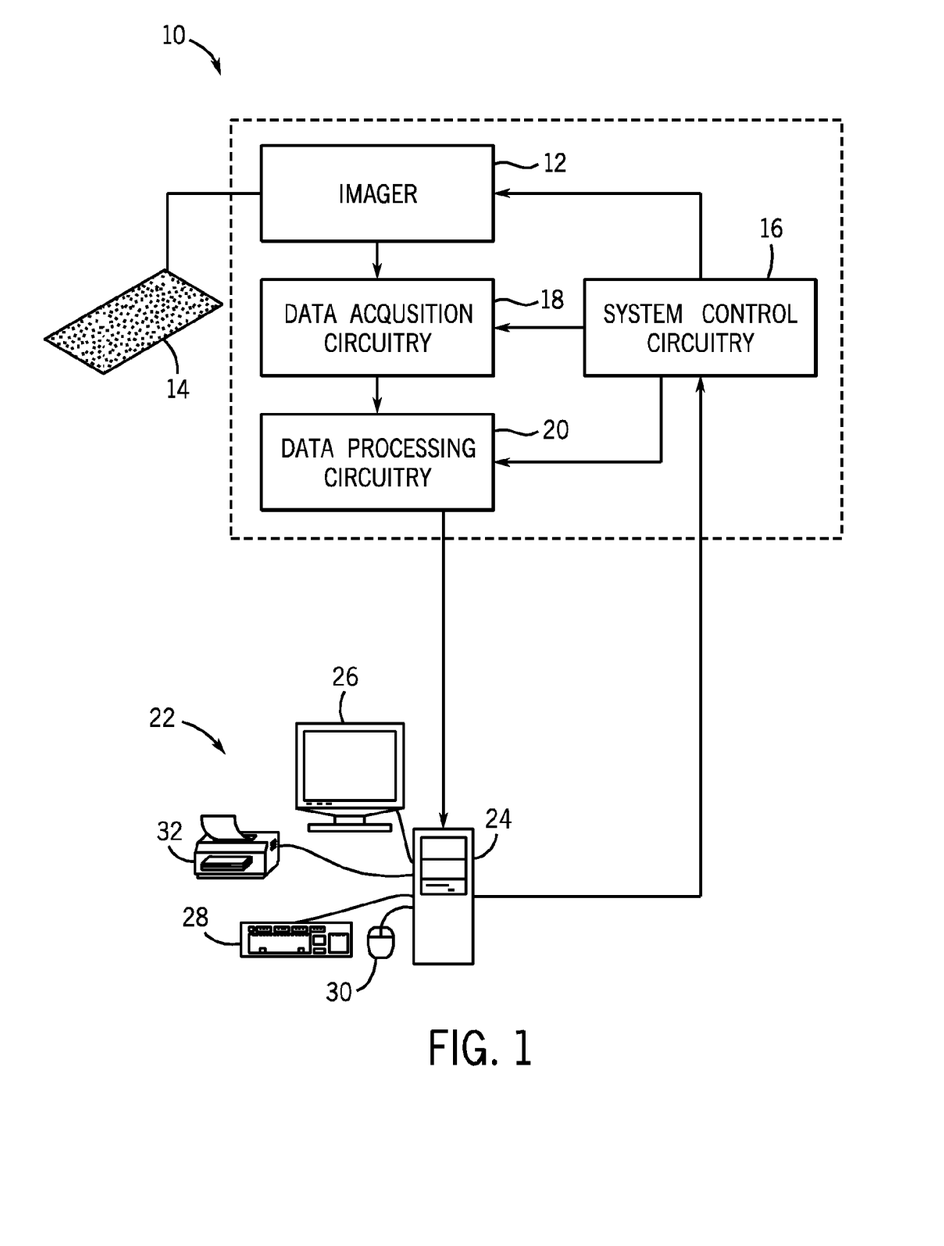
FIG. 1 is a diagrammatical view of an exemplary system for use in acquiring image data of TMAs in accordance with aspects of the present technique.

The present techniques provide systems and methods for image analysis. In certain embodiments, it is envisioned that the present techniques may be used in conjunction with previously acquired images, for example, digitally stored images, in retrospective studies. In other embodiments, the images may be acquired from a physical sample. In such embodiments, the present techniques may be used in conjunction with an image acquisition system. An exemplary imaging system 10 capable of operating in accordance with the present technique is depicted in FIG. 1. Generally, the imaging system 10 includes an imager 12 that detects signals and converts the signals to data that may be processed by downstream processors. The imager 12 may operate in accordance with various physical principles for creating the image data and may include a fluorescent microscope, a bright field microscope, or devices adapted for suitable imaging modalities. In general, however, the imager 12 creates image data indicative of a biological sample including a population of cells 14, shown here as being multiple samples on a tissue microarray. The image may be a digital image or a film image. As used herein, the term "biological material" or "biological sample" refers to material obtained from, or located in, a biological subject, including biological tissue or fluid obtained from a subject. Such samples may be, but are not limited to, body fluid (e.g., blood, blood plasma, serum, or urine), tissues, fractions, and cells isolated from, or located in, any biological system, such as mammals. Biological samples and/or biological materials also may include sections of the biological sample including tissues (e.g., sectional portions of an organ or tissue). Biological samples may also include extracts from a biological sample, for example, a subpopulation of cells from a biological fluid (e.g., blood or urine).

The imager 12 operates under the control of system control circuitry 16. The system control circuitry 16 may include a wide range of circuits, such as illumination source control circuits, timing circuits, circuits for coordinating data acquisition in conjunction with sample movements, circuits for controlling the position of light sources and detectors, and so forth. In the present context, the system control circuitry 16 may also include computer-readable memory elements, such as magnetic, electronic, or optical storage media, for storing programs and routines executed by the system control circuitry 16 or by associated components of the system 10. The stored programs or routines may include programs or routines for performing all or part of the present technique.

Image data acquired by the imager 12 may be processed by the imager 12, for a variety of purposes, for example to convert the acquired data or signal to digital values, and provided to data acquisition circuitry 18. The data acquisition circuitry 18 may perform a wide range of processing functions, such as adjustment of digital dynamic ranges, smoothing or sharpening of data, as well as compiling of data streams and files, where desired.

The data acquisition circuitry 18 may also transfer acquired image data to data processing circuitry 20, where additional processing and analysis may be performed. Thus, the data processing circuitry 20 may perform substantial analyses of image data, including ordering, sharpening, smoothing, feature recognition, and so forth. In addition, the data processing circuitry 20 may receive data for one or more sample sources, (e.g. multiple TMA slides). The processed image data may be stored in short-term or long-term storage devices, such as picture archiving communication systems, which may be located within or remote from the imaging system 10 and/or reconstructed and displayed for an operator, such as at the operator workstation 22.

In addition to displaying the reconstructed image, the operator workstation 22 may control the above-described operations and functions of the imaging system 10, typically via an interface with the system control circuitry 16. The operator workstation 22 may include one or more processor-based components, such as general purpose or application-specific computers 24. In addition to the processor-based components, the computer 24 may include various memory and/or storage components including magnetic and optical mass storage devices and/or internal memory, such as RAM chips. The memory and/or storage components may be used for storing programs and routines for performing the techniques described herein that are executed by the operator workstation 22 or by associated components of the system 10. Alternatively, the programs and routines may be stored on a computer accessible storage medium and/or memory remote from the operator workstation 22 but accessible by network and/or communication interfaces present on the computer 24.

The computer 24 may also comprise various input/output (I/O) interfaces, as well as various network or communication interfaces. The various I/O interfaces may allow communication with user interface devices, such as a display 26, keyboard 28, mouse 30, and printer 32, that may be used for viewing and inputting configuration information and/or for operating the imaging system 10. The various network and communication interfaces may allow connection to both local and wide area intranets and storage networks as well as the Internet. The various I/O and communication interfaces may utilize wires, lines, or suitable wireless interfaces, as appropriate or desired.

More than a single operator workstation 22 may be provided for an imaging system 10. For example, an imaging scanner or station may include an operator workstation 22 which permits regulation of the parameters involved in the image data acquisition procedure, whereas a different operator workstation 22 may be provided for manipulating, enhancing, and viewing results and reconstructed images.

Figure 2:
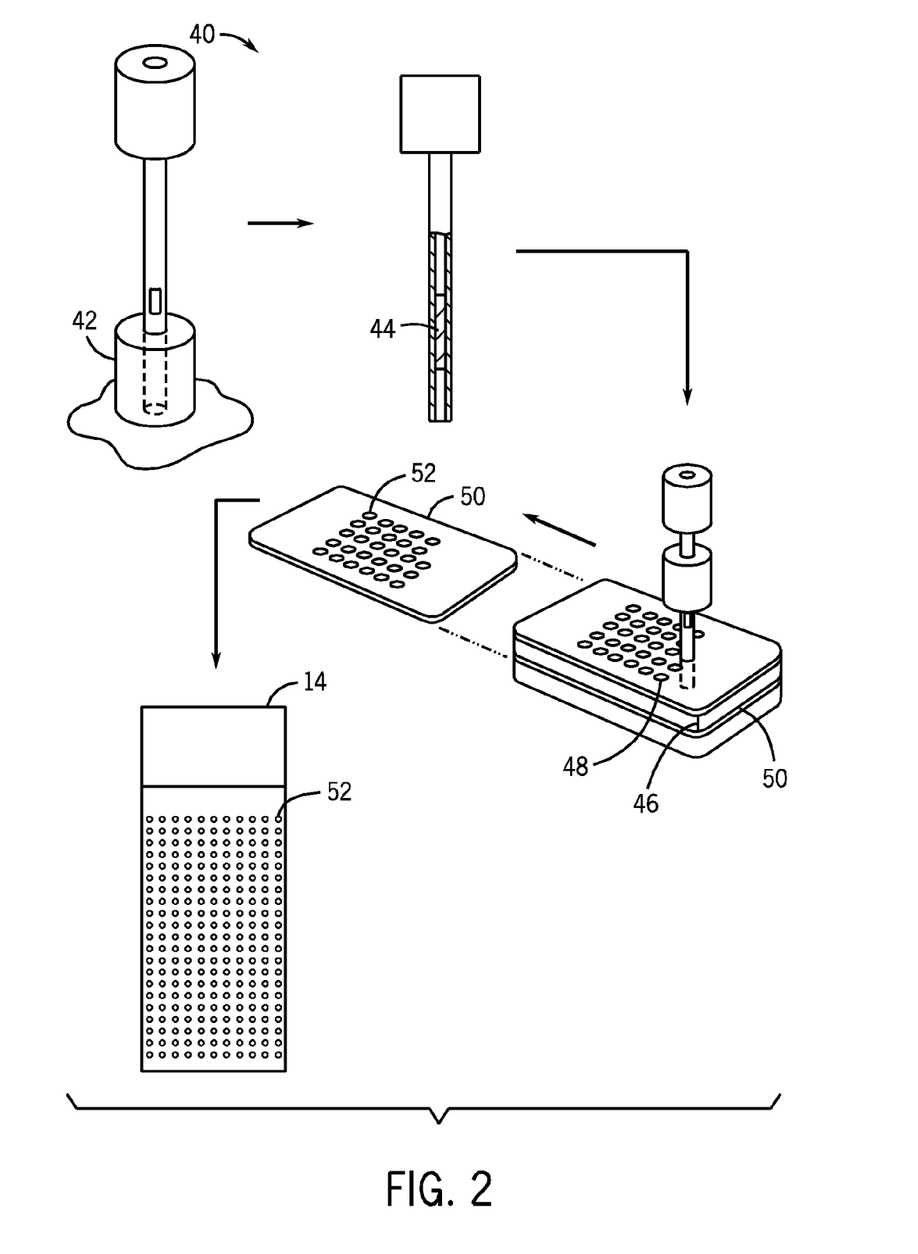
FIG. 2 is a process diagram depicting a process for producing TMA serial sections in accordance with aspects of the present technique.

FIG. 2 shows an exemplary process 40 for the preparation of a TMA slide 14, such as may be imaged by the system of FIG. 1, in accordance with the present techniques. In certain embodiments, TMA slides may be prepared by obtaining multiple tissue cores 44. For example, a tissue core 44 may be a section about 0.6 mm in diameter that is obtained from the patient tissue block 42 (i.e., the "donor block") and inserted in a pre-determined grid location on an initially blank paraffin block 46 (i.e., the "recipient block"). The resulting finished recipient block 46 may have hundreds of tissue cores from multiple patients, with each patient contributing more than one core in certain embodiments. This recipient tissue block may then be cut into sections 50 that may be placed on any suitable substrate for examination and imaging. The sections 50 each include a number of tissue spots 52 that each represents a portion of a respective tissue core 44. In this manner, a number of TMA slides 14 may be made from a recipient block 46. In each of the serial sections made into TMAs, corresponding tissue spots 52 belong to the same tissue core 44, i.e., the same patient sample.

The present techniques allow corresponding tissue spots 52 to be matched up with each other and with clinical information about the tissue core 44 and/or the patient from whom the tissue core 44 was obtained. Such clinical information may include, for example, patient identification information, patient identification numbers, diagnosis information, treatment information, medical history information, biochemical information, physiologic information, family history information, patient dietary information, patient exercise information, demographic information, or drug response information. The clinical information also may include genotype information or haplotype information, such as a chromosome structure, a DNA sequence, a length of a specific gene or region, a gene expression, or at least one single nucleotide polymorphism (SNP). In another embodiment, the clinical information may include information related to one or more clinical trials. In one embodiment, the clinical information may include information related to the tissue core 44, such as tissue type, pathological information, and information about the preparation and storage procedures related to the tissue core 44.

Figure 3:
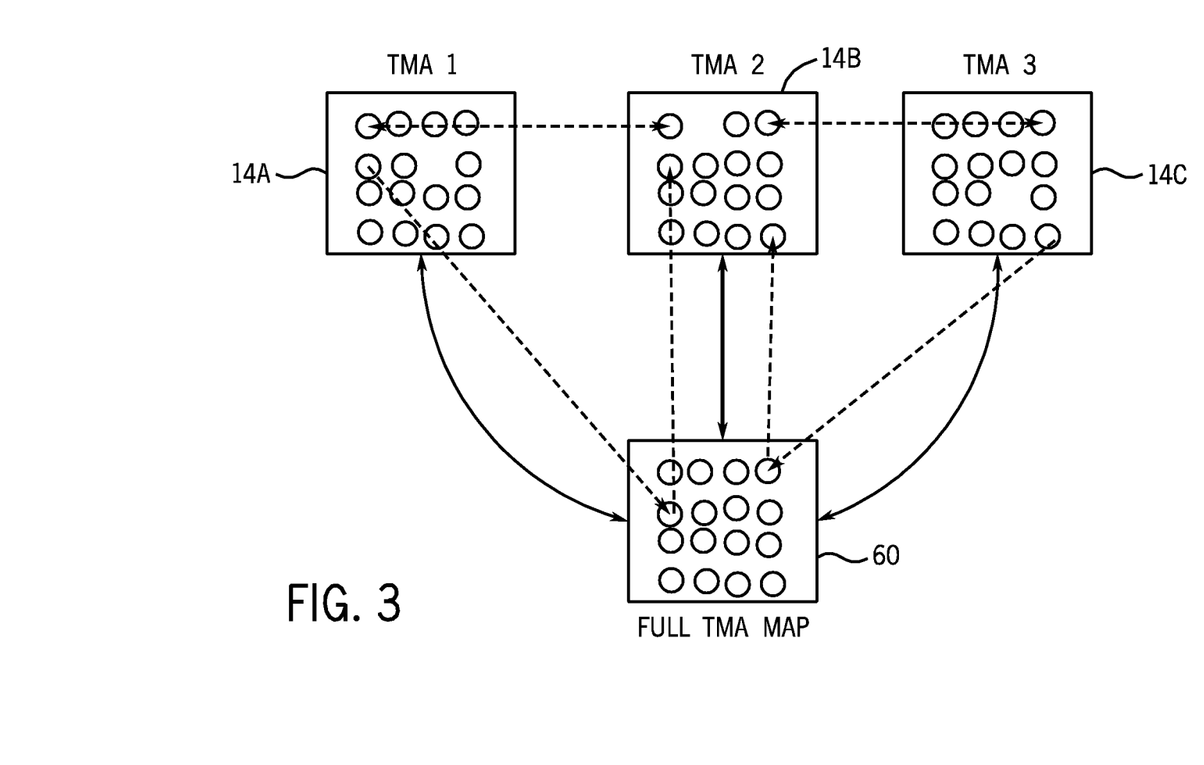
FIG. 3 is an overview of an exemplary process for use in determining the correspondence of tissue spots on multiple TMAs in accordance with aspects of the present technique.

FIG. 3 is a general overview of certain methods for matching TMA tissue spots 52 with other TMAs in accordance with the present techniques. TMA tissue spots 52 that are taken from the same tissue core 44 in serial sections of a recipient block 46 correspond to one another. Each tissue core 44 on a recipient block 46 may be referred to by row and column number, or by any suitable identification mechanism. A TMA 14 may be matched (i.e., analyzed for tissue spot correspondence) with one or more adjacent TMA sections derived from the same recipient block 46 and/or with a full TMA map 60. The full TMA map 60 may be generated by using an image of a TMA 14 that either has no missing tissue spots 52 or in which the missing tissue spots have been filled in with data from other TMA sections. In addition, the full TMA map 60 may include reference information for each tissue spot that includes a row number and a column number. By matching a given TMA 14 to the full TMA, 60 the row and column indices of each spot may be obtained, and may be correlated with spots in other TMAs. Since the number of rows and columns are constant between TMAs from the same recipient block, they may be used as a key for relating tissue spots 52 in multiple TMAs to the original tissue cores 44.

Figure 4:
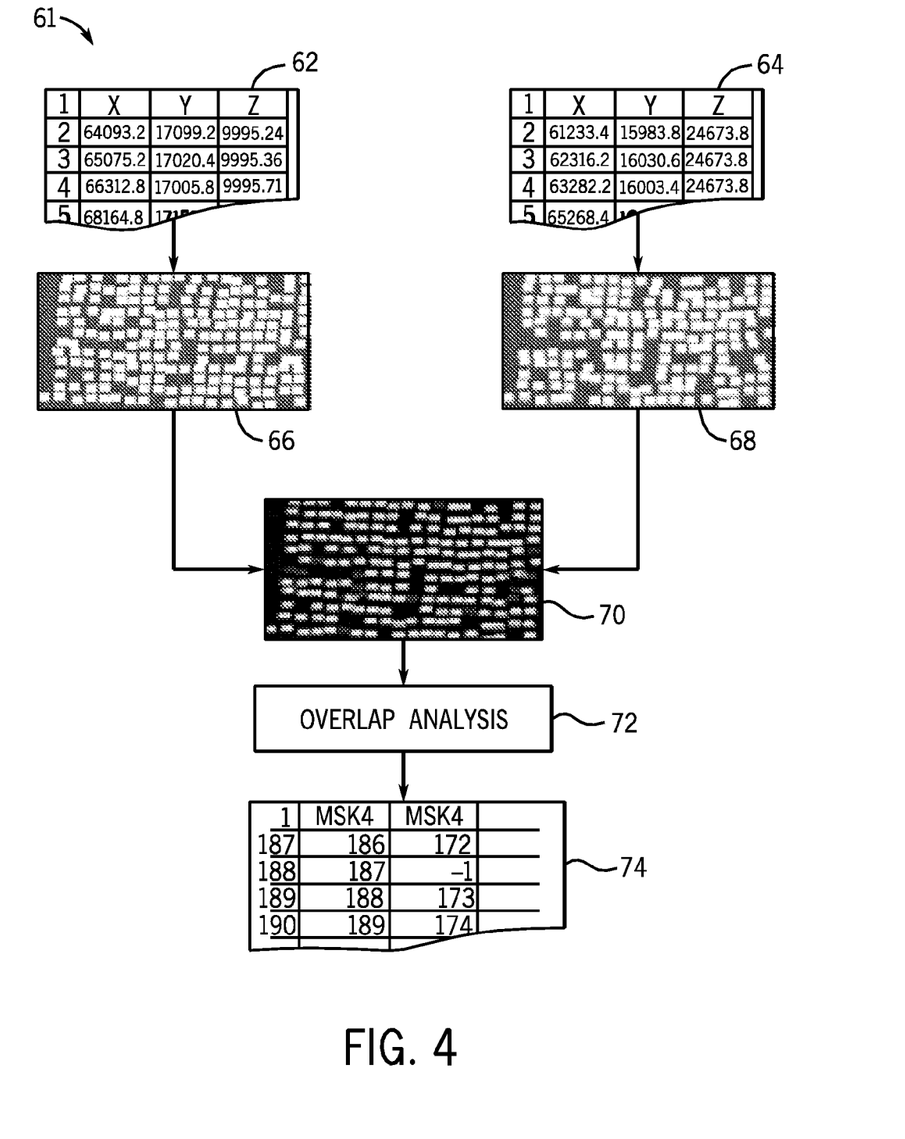
FIG. 4 is a process diagram depicting a process for analyzing TMAs in accordance with the present technique.

FIG. 4 is a flowchart showing a method 61 of directly comparing two TMA slides (with x-y coordinates 62 and 64) with one another. Given the coordinates of tissue spots 52 in two TMAs, the spots may be matched in three steps: (i) simulation of images of TMA slides from the coordinates if a whole slide is not available (simulated images 66 and 68); (ii) rigid registration of the two simulated slide images 66 and 68 to form registered image 70; and (iii) determination of overlap extent of the spots and identification of missing spots in step 72.

With regard to step (i), in embodiments when a whole slide image is not available, a TMA slide may be simulated from the x-y coordinates of the tissue spots 52 of an individual TMA 14. For example, a simulated image (e.g. image 66 or 68) may be created as a gray background with white spots (e.g., for fluorescent microscopy applications) or gray spots on a white background for (e.g., for bright field applications). In one embodiment, rectangles are used to represent the tissue spots 52 on the slide, though circles or the actual subsampled images may also be used. The rectangles may be centered at the locations specified by the x-y coordinates. The size of each rectangle and the overall size of the TMA slide may be user-configurable, but may be equal in any TMAs 14 that will be registered with one another. Choices of the size of the rectangle and the size of the TMA slide may affect the relative spacing between the tissue spots and may be chosen to avoid overlap of the rectangles between spots adjacent to one another on a TMA 14. The output of the simulation step is two simulated TMA slides (e.g. image 66 or 68) representing the layout of tissue spots on each TMA. In another embodiment (not shown), whole slide images from the two serial sections may be used for the image registration.

Image registration may be performed in order to determine spot-to-spot correspondence between the two TMAs by analyzing the overlap of the tissue spots 52 after registration. Any suitable image registration technique may be used, such as mutual information or correlation-based techniques, to register the whole slide images or simulated images of the TMA slides. In one embodiment, a mutual-information metric may be used. The mutual information metric provides the advantage of being robust across different image modalities, allowing registration of bright field with fluorescent images. A rigid registration framework may be advantageous because the two TMAs are from the same recipient block and, thus, no significant non-rigid deformation is expected from one section to another.

Given two TMA slide images (simulated or scanned), $I^{(1)}(x,y)$ and $I^{(2)}(x,y)$, a transformation $T^{2,1}$, such that the image similarity measure between $I^{(1)}(x,y)$ and $I^{(2)}(T^{2,1}(x,y))$, is maximized. A mutual information metric my be used to maximize:

$$S(t) = -\sum_l \sum_\kappa p(l,\kappa \mid t) \log \frac{p(l,\kappa \mid t)}{p_M(l \mid t) p_F(\kappa)} \quad (1)$$

where $p$, $p_M$, and $p_F$ are the joint, marginal moving, and marginal fixed probability distribution of the image intensities; $t$ is the parameter vector of the transform; $\tau$ and $\kappa$ are the intensity values in the respective slide images. In one embodiment, a multi-resolution strategy may be used to find the transform that aligns the two images 66 and 68. Once a registration solution is identified, the registered images may be physically overlaid, with each simulated slide image put in a different RGB channel to generate an intermediate colored image of the overlaid TMA slides. This overlaid slide image may be used for visual verification of the registration solution.

Figure 5A:
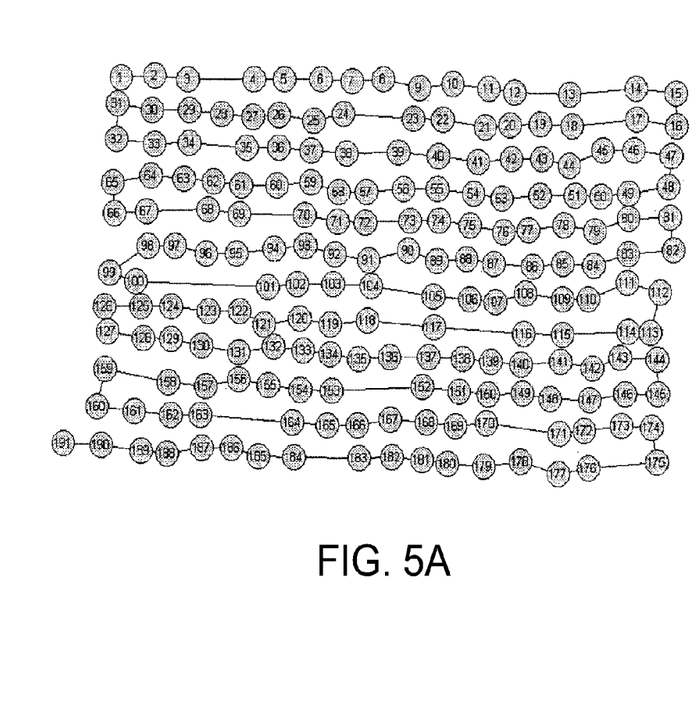
FIG. 5A is a schematic representation of the tissue spots on an individual TMA, in accordance with aspects of the present technique.
Figure 5B:
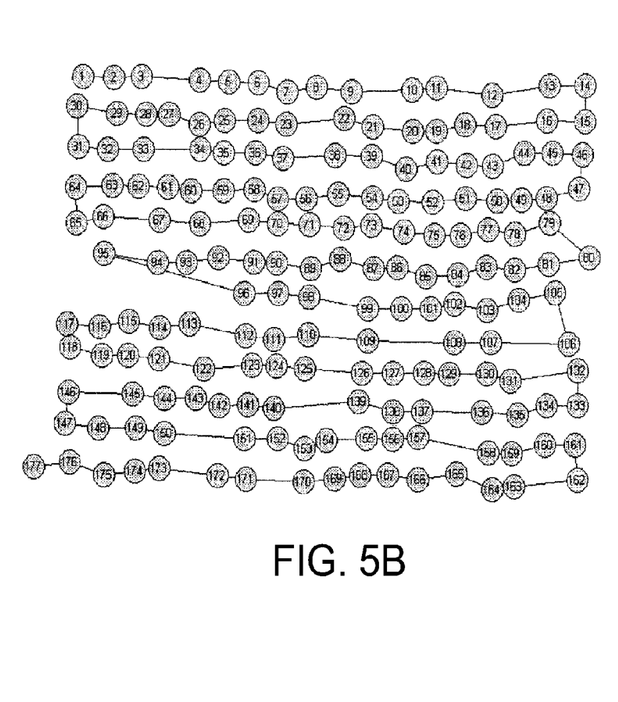
FIG. 5B is a schematic representation of the tissue spots on an adjacent TMA to the TMA of FIG. 5A in accordance with aspects of the present technique.

After registration, correspondence may be determined for tissue spots 52 between the two or more TMAs. Correspondence may be determined by analyzing the position of a particular spot 52 and its overlap with a spot 52 on another TMA. If a spot 52 has substantial overlap with only one other spot 52, they likely correspond. For some tissue spots 52, there is overlap with two or more tissue spots 52 in the other TMA. For these tissue spots 52, correspondence may be determined by examining the areas of overlap between the spots. For example, in one embodiment a tissue spot 52 may be determined to correspond if it has greater overlap with a tissue spot 52 in the second TMA, subject to a minimum overlap ratio of 33% of the spot area. Since the coordinates are recorded in the order in which the images are scanned (a serpentine pattern, see FIGS. 5A and 5B), in one embodiment, the correspondence may be determined by considering only tissue spots 52 spots on the same row in the second TMA. This excludes tissue spots 52 on the previous or subsequent rows, even when there is overlap. A new row is identified by a change in the direction of the x-coordinates. Similarly, missing tissue spots are identified as tissue spots 52 without any overlap with tissue spots 52 in the other TMA (or with overlap less than the minimum allowable overlap ratio). In case a correspondence is not determined automatically, the tissue spot 52 may be flagged for manual examination by the user.

In one embodiment, the output of the correspondence analysis 72 is a spreadsheet file 74. For example, a spreadsheet file 74 may be generated with each row having the image number from the first TMA and the corresponding image number from the second TMA. The image numbers may be the serial numbers automatically assigned to each image by the microscope. The full image names can also be included if desired. In certain embodiments, a numerical flag, for example −1, may be used to indicate missing tissue spots 52. In other embodiments, missing spots 52 may be indicated by "BLANK" or any suitable text indicator.

Figure 6:
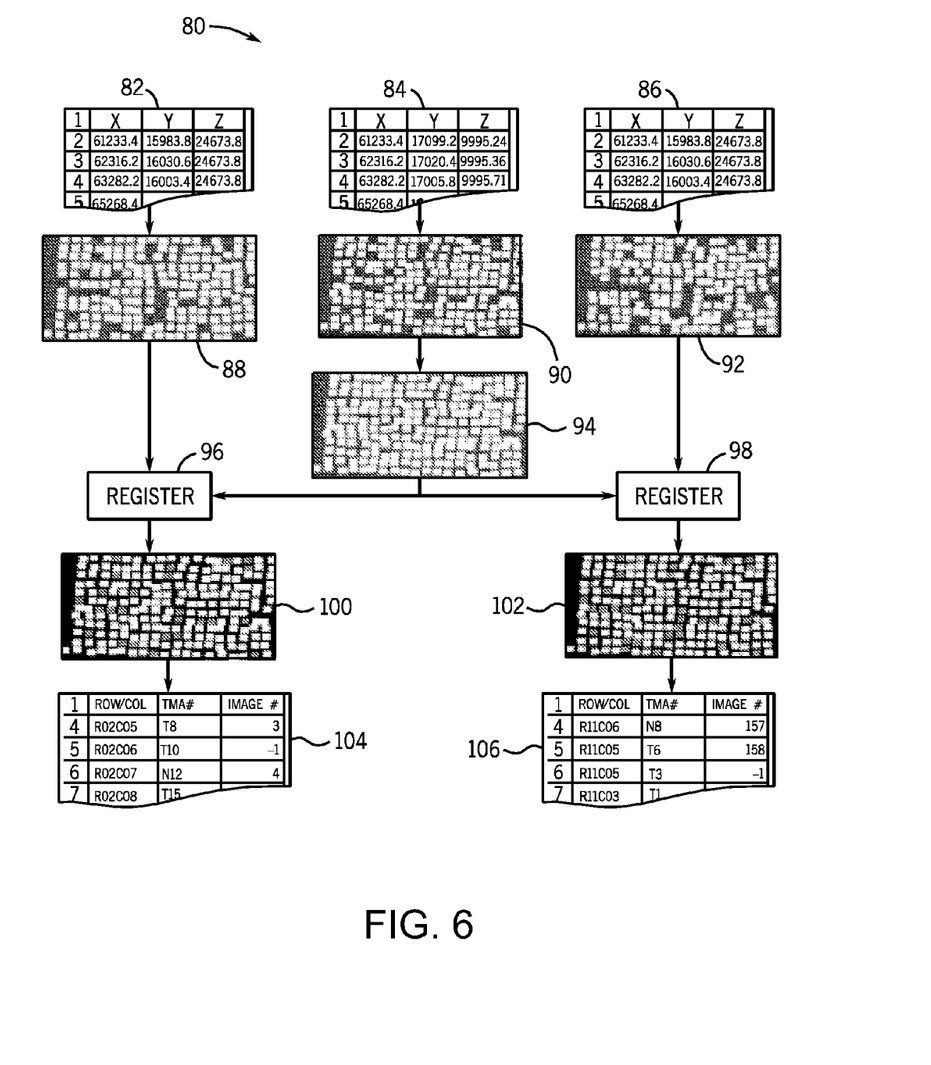
FIG. 6 is a process diagram depicting an alternative process for analyzing TMAs in accordance with the present technique.

An alternative embodiment, shown in FIG. 6, may be used in cases in which there are more than two TMAs 14 to be analyzed. Using either the x-y coordinates of multiple TMAs (coordinates 82, 84, and 86), or, alternatively, whole-slide images (not shown), a full TMA 94 may be generated that represents the block. From coordinates 82, 84, and 86, respectively, simulated TMAs 88, 90, and 92 may be generated. The simulated TMA with the fewest or no missing spots, for example simulated TMA 90, may be used to interpolate any missing spots to make a full TMA 94. For very complex arrangements of tissue spots 52, the missing spots may be interpolated manually. The full TMA 94 has no spots 52 missing, and each spot has a clearly defined row and column index. The full TMA 94 may be used to individually match each of the other TMAs 14. By matching a given TMA 14 to the full TMA 94, the row and column indices of each spot is obtained, and may be used to determine correspondence with tissue spots 52 in other TMAs. During the registration step (steps 96 and 98), the individual TMAs 14 are registered with the full TMA 94 to generate outputs 104 and 106, respectively.

EXAMPLES

The following examples illustrate embodiments of the present techniques. In one example, ten TMA slides from a recipient tissue block, originally consisting of 217 breast tissue cores from 55 patients, were analyzed. Six of the slides were conjugated with immuno-fluorescent (IF) dyes and examined under fluorescent microscopy. The remaining four slides were examined with bright field microscopy after diaminobenzidine tetrahydrochloride (DAB) staining. The whole slide scan was not available for the DAB slides and one of the IF slides. Pathologists provided a TMA-map (shown in FIG. 7D) for the block. Serial numbers were automatically assigned to the images during scanning for identification. The tissue spots on four of the IF slides were labeled with AR, ER, p53, and Her2 biomarkers respectively and cores on the remaining two were used for multiplexing with multiple biomarkers. The DAB stains were also used to test for the same four biomarkers under bright field microscopy.

Figure 8A:
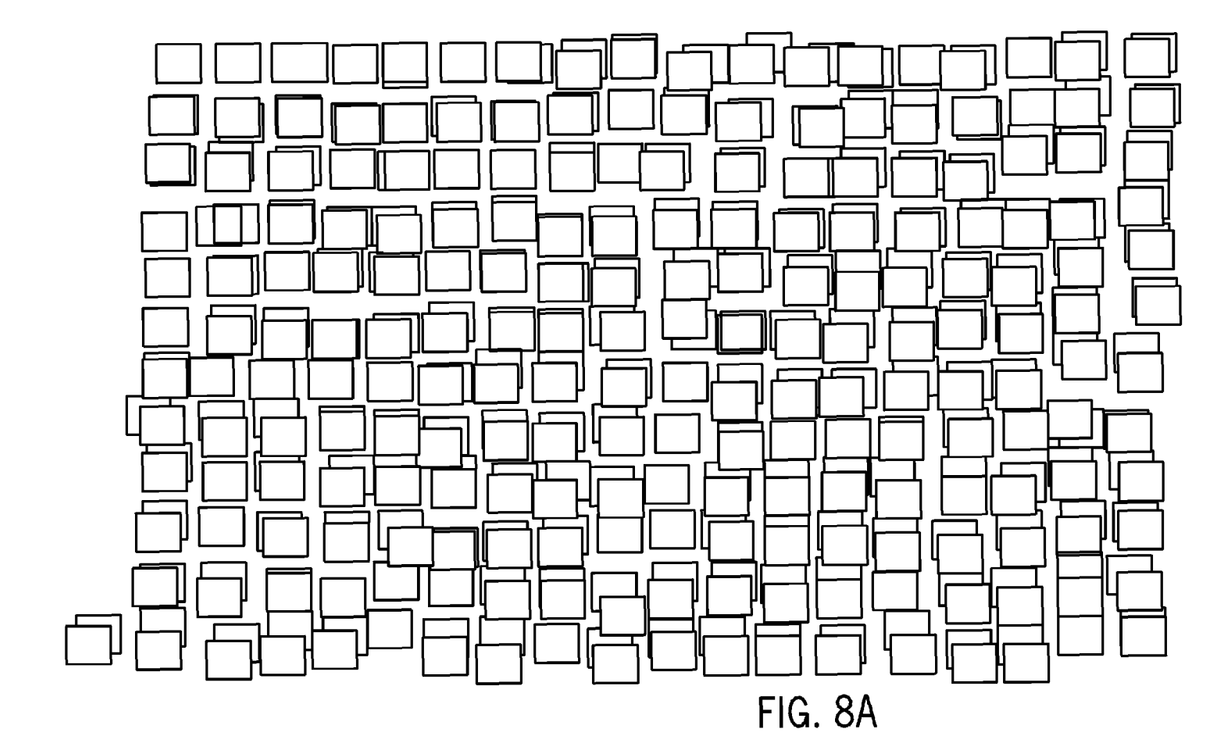
FIG. 8A is an exemplary matched TMA that may be verified by an operator in accordance with aspects of the present technique.
Figure 8B:
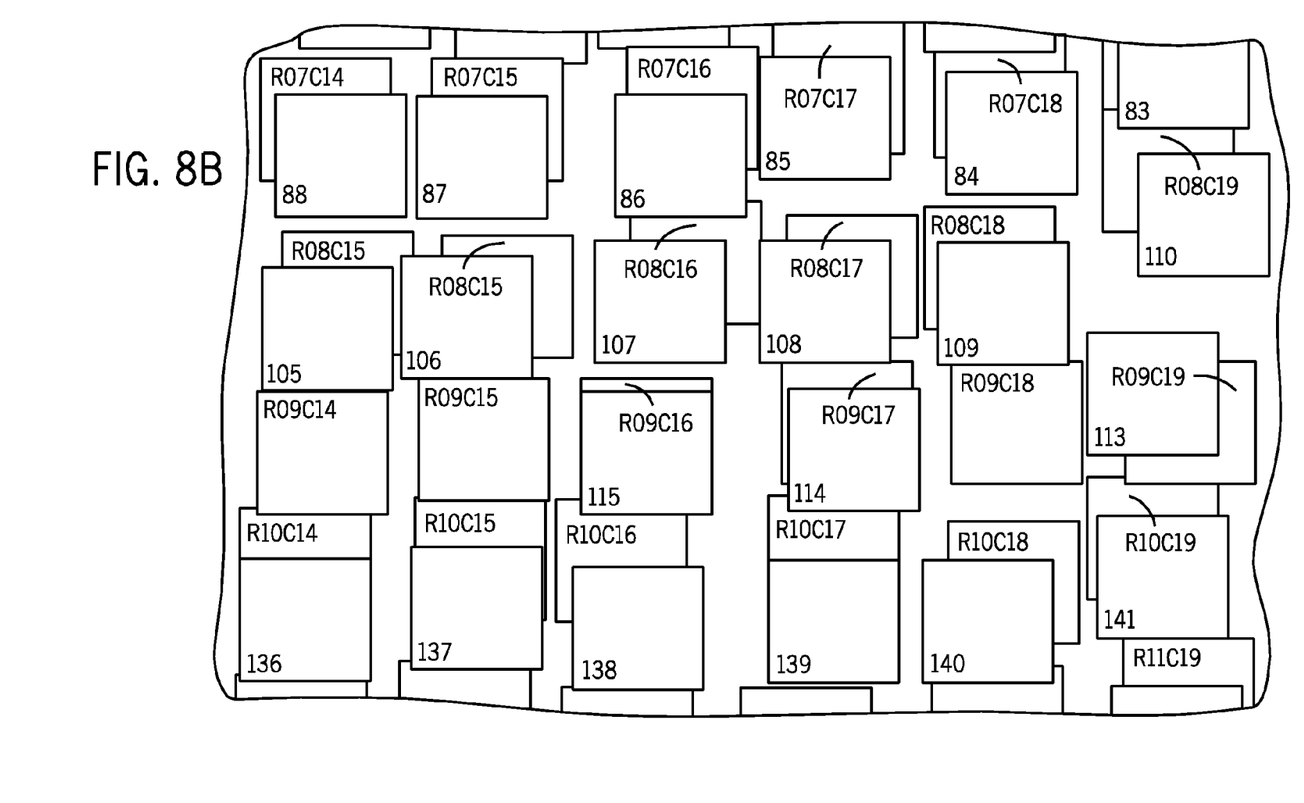
FIG. 8B is an enlarged view of the matched TMA of FIG. 7A in accordance with aspects of the present technique.
Figure 9:
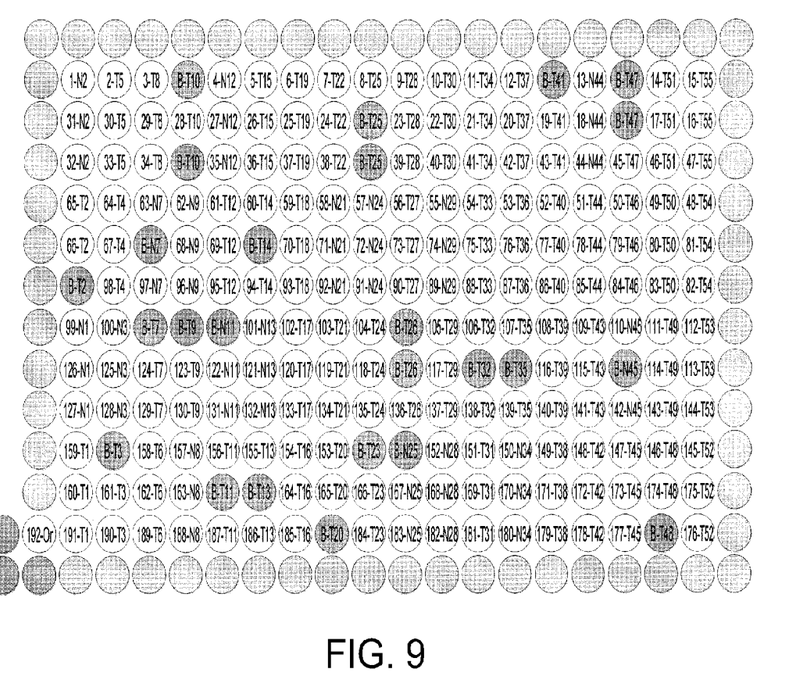
FIG. 9 is an exemplary matched TMA output in which the tissue spots are marked with image and TMA numbers in accordance with aspects of the present technique.

After analysis, all tissue spots 52 were matched across all the TMAs with 100% accuracy. The TMAs were similarly matched with the TMA-map, and hence clinical information, without any error. The process of matching one TMA to another took about 45 seconds (with 30 seconds accounting for the registration alone) on a Pentium M Windows PC. Visual images of the overlaid TMAs (FIGS. 8A and 8B, FIG. 9) were generated for verification along with the spreadsheet file that listed the tissue spot correspondences. In one embodiment, the full TMA may be indicated in a first color channel while the TMA matched to the full TMA may be indicated in a second color channel in order to more easily distinguish between the two overlaid images (FIGS. 8A and 8B). Additionally, certain areas may be flagged for user verification, for example, in a case where one spot overlaps with multiple tissue spots on another TMA. In one embodiment, the output of a matched TMA, as shown in FIG. 9, may include information about the tissue spot and indicators to indicate blank tissue spots and identify the missing spots. For example, blank spots are indicated in FIG. 9 with a "B" followed a tissue core identifier.

To relate tissue spots on a TMA with clinical information, a TMA map (FIG. 7D) was used. The TMA map is shown as a grid representing the positions of the tissue cores on the recipient block and does not have any missing spots. Each element was assigned a TMA number that was also included in relevant clinical information files, along with patient ID, case code, tissue block ID, and pathologists scores. The present techniques allow the operator to automatically relate the image numbers obtained from the microscope with the TMA numbers provided by pathologists. The correlation was performed by simulating a full TMA (without missing tissue spots) and then matching tissue spots in the full TMA to the desired TMA as described. A full TMA was generated by interpolating missing tissue spots on the most complete TMA (i.e., with the highest number of tissue spots) in the block. Selecting the most complete TMA reduced the number of tissue spots 52 that were interpolated. Interpolation may also be performed manually, especially when the layout of the tissue spots on the slide is irregular.

Figure 7A:
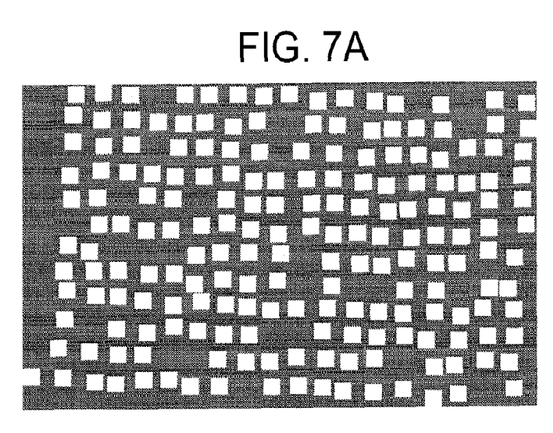
FIG. 7A is a simulated layout of the tissue spots on a TMA, Serial Section 2, in accordance with aspects of the present technique.
Figure 7B:
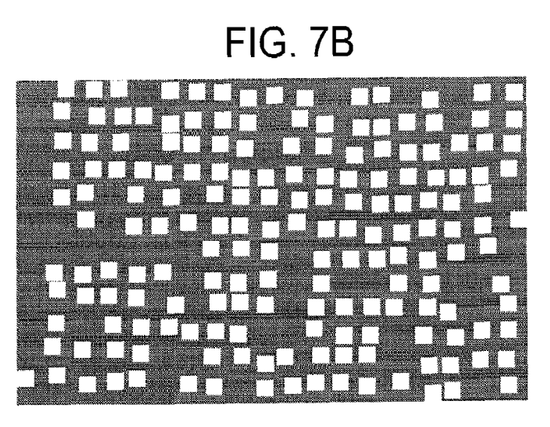
FIG. 7B is a simulated layout of the tissue spots on a TMA, Serial Section 1, in accordance with aspects of the present technique.

The coordinates of the spots were recorded in the order of acquisition in a serpentine pattern, starting with the leftmost spot to the rightmost spot in the first row, then from rightmost to leftmost in the second row, etc. (see FIGS. 5A and 5B). The knowledge of the order of scanning was used to help determine the approximate distance between rows and columns. FIGS. 7A and 7B show simulated images for two TMAs from the same recipient block. FIG. 7A shows a simulated TMA (referred to as Serial Section 2) with 191 spots simulated based on the x-y microscope coordinates of the tissue spots. FIG. 7B shows a simulated TMA (referred to as Serial Section 1) with 177 spots simulated based on the x-y microscope coordinates of the tissue spots. The distance $\Delta x$ was determined between the x-coordinates of consecutive tissue spots. Based on the numerical values, each of the $\Delta x$ distances were assigned to one of three clusters: (i) a normal distance between adjacent tissue spots on the same row when no tissue spots are missing; (ii) a relatively large distance between tissue spots when one or more tissue spots are missing; and (iii) a relatively small distance between tissue spots in the same column at the beginning and end of rows. The magnitude of each difference was determined in the x-coordinate, $|\Delta x_i|$, and automatically clustered into three groups. The cluster that had the median value of $|\Delta x_i|$, was defined as the group with normal inter-spot distances. This assumed that cases of normal inter-spot distances were more than 50% of all cases. This assumption was verified by confirming that the cluster with the median value of $|\Delta x_i|$ also had the largest number of tissue spots. The mean inter-spot distance for this group was then used to estimate the number of columns in the TMA by considering the tissue spots at the extreme ends of the rows.

Since the images on the TMA were scanned in a zigzag pattern, a change in sign of $\Delta x$ is used to determine the beginning of a new row. The magnitude of $\Delta x$ for the spot before and after the change in sign still was examined to assign a particular spot to the beginning of the row. By examining the cluster that these tissue spots belong to, the actual beginning or end of the row was determined, and the total number of rows counted. In cases of missing tissue spots, it was determined if these spots were at the beginning or end of rows likewise.

By examining each of the $|\Delta x_i|$ belonging to the third cluster, the number of missing tissue spots between two consecutive tissue spots was estimated by dividing the distance with the average normal inter-spot distance. The average y-coordinates of adjacent tissue spots were used for the interpolated tissue spots, and $|\Delta x_i|$ were divided equally to accommodate all the interpolated missing tissue spots.

Figure 7C:
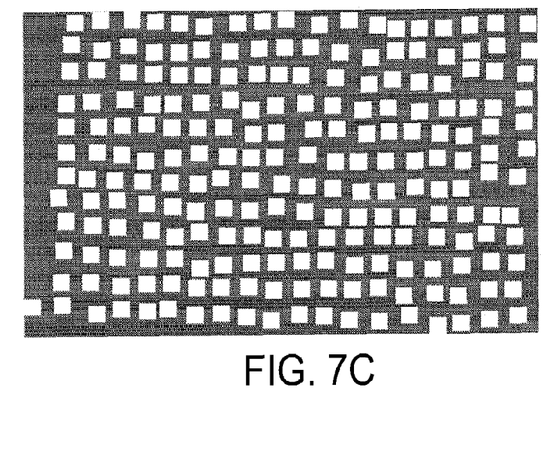
FIG. 7C is a simulated full TMA from the same recipient block as in FIGS. 6A and B in which any missing spots have been extrapolated in accordance with aspects of the present technique.
Figure 7D:
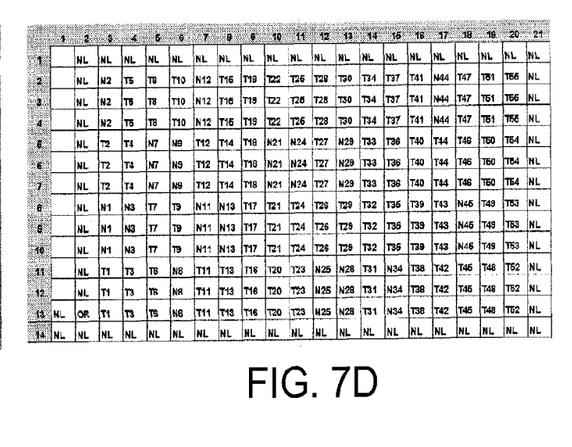
FIG. 7D is TMA map of the recipient block in accordance with the present technique.

Once the missing tissue spots were interpolated, a full TMA was simulated (FIG. 7C) with missing spots interpolated for a total of 217 tissue spots. A row and column number were assigned to each spot. The assigned rows and columns corresponded directly to those in the TMA map in FIG. 7D, creating a direct relation between the full TMA and the pathologist-supplied TMA map. Any given TMA was then able to be matched to the full TMA. After the matching, the row and column numbers of each spot in the TMA, and hence the TMA number were obtained directly from the full TMA. This related each spot to the TMA numbers (FIG. 9), and consequently to clinical information. Note that the above process may be simplified if the number of rows and columns in the TMA is known a priori.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for analyzing tissue microarrays using a computer, comprising the steps of:
   accessing coordinate data for two or more tissue microarrays using the computer, wherein the tissue microarrays are derived from the same recipient block, and wherein the coordinate data comprises coordinates of a respective plurality of tissue spots within the respective two or more tissue microarrays;
   generating on the computer two or more respective simulated images based on the coordinate data of the respective plurality of tissue spots;
   comparing the two or more simulated images on the computer to correlate the position of each of the respective plurality of tissue spots of the tissue microarrays with one another; and
   generating an output on the computer relating the position of the tissue spots of the two or more tissue microarrays based on the analyzed positions, wherein the output comprises identification information or a grid position for each of the respective plurality of tissue spots.

2. The method of claim 1, comprising determining which tissue spots are missing from the tissue microarrays.

3. The method of claim 1, comprising assigning each of the tissue spots on a given tissue microarray an identity based on its correspondence to a master map of the recipient block or to a designated master tissue microarray from the same recipient block.

4. The method of claim 3, wherein assigning the identity comprises assigning clinical information.

5. The method of claim 1, wherein the generating the output comprises representing the position of the tissue spots in a common coordinate system.

6. The method of claim 5, wherein generating the common coordinate system comprises row and column numbers based on a master map of a recipient donor block.

7. The method of claim 1, wherein analyzing the position of each of the respective plurality of tissue spots comprises analyzing the overlap of the tissue spots.

8. A non-transitory computer-readable medium comprising instructions for:
- accessing coordinate data for two or more tissue microarrays, wherein the tissue microarrays are derived from the same recipient block, and wherein the coordinate data comprises coordinates of a respective plurality of tissue spots within the respective two or more tissue microarrays;
- generating two or more respective simulated images based on the coordinate data of the respective plurality of tissue spots;
- comparing the two or more simulated images to correlate the position of each of the respective plurality of tissue spots of the tissue microarrays with one another; and
- generating an output relating the position of the tissue spots of the two or more tissue microarrays based on the analyzed positions, wherein the output comprises identification information or a grid position for each of the respective plurality of tissue spots.

9. The non-transitory computer-readable medium of claim 8, comprising determining which tissue spots are missing from the tissue microarrays.

10. The non-transitory computer-readable medium of claim 8, comprising assigning each of the tissue spots on a given tissue microarray an identity based on its correspondence to a master map of the recipient block or to a designated master tissue microarray from the same recipient block.

11. The non-transitory computer-readable medium of claim 10, wherein assigning the identity comprises assigning clinical information.

12. The non-transitory computer-readable medium of claim 8, wherein the generating the output comprises representing the position of the tissue spots in a common coordinate system.

13. The non-transitory computer-readable medium of claim 12, wherein generating the common coordinate system comprises row and column numbers based on a master map of a recipient donor block.

14. The non-transitory computer-readable medium of claim 8, wherein analyzing the position of each of the respective plurality of tissue spots comprises analyzing the overlap of the tissue spots.

15. An image analysis system comprising:
- a processor adapted to receive coordinate data for two or more tissue microarrays, wherein the tissue microarrays are derived from the same recipient block, and wherein the coordinate data comprises coordinates of a respective plurality of tissue spots within the respective two or more tissue microarrays, the processor adapted to run instructions for:
- generating two or more respective simulated images based on the coordinate data of the respective plurality of tissue spots;
- comparing the two or more simulated images to correlate the position of each of the respective plurality of tissue spots of the tissue microarrays with one another; and
- generating an output relating the position of the tissue spots of the two or more tissue microarrays based on the analyzed positions, wherein the output comprises identification information or a grid position for each of the respective plurality of tissue spots.

16. The image analysis system of claim 15, comprising determining which tissue spots are missing from the tissue microarrays.

17. The image analysis system of claim 15, comprising assigning each of the tissue spots on a given tissue microarray an identity based on its correspondence to a master map of the recipient block or to a designated master tissue microarray from the same recipient block.

18. The image analysis system of claim 17, wherein assigning the identity comprises assigning clinical information.

* * * * *